United States Patent
Lau et al.

(10) Patent No.: US 11,311,227 B2
(45) Date of Patent: *Apr. 26, 2022

(54) FETAL ECG AND HEART RATE ASSESSMENT AND MONITORING DEVICE

(71) Applicant: Sensoriis, Inc., Edmonds, WA (US)

(72) Inventors: Michael P. H. Lau, Edmonds, WA (US); Hung V. Cao, Kenmore, WA (US)

(73) Assignee: Sensoriis, Inc., Edmonds, WA (US)

( * ) Notice: Subject to any disclaimer, the term of this patent is extended or adjusted under 35 U.S.C. 154(b) by 138 days.

This patent is subject to a terminal disclaimer.

(21) Appl. No.: 16/748,549

(22) Filed: Jan. 21, 2020

(65) Prior Publication Data

US 2020/0155027 A1 May 21, 2020

Related U.S. Application Data

(63) Continuation of application No. 15/787,371, filed on Oct. 18, 2017, now Pat. No. 10,575,747.

(Continued)

(51) Int. Cl.
*A61B 5/00* (2006.01)
*A61B 5/288* (2021.01)
(Continued)

(52) U.S. Cl.
CPC .......... *A61B 5/288* (2021.01); *A61B 5/02427* (2013.01); *A61B 5/02438* (2013.01);
(Continued)

(58) Field of Classification Search
CPC ......... A61B 5/288; A61B 5/282; A61B 5/327; A61B 5/02444; A61B 5/7235; A61B 5/02427; A61B 5/02438; A61B 5/339; A61B 5/389; A61B 5/6823; A61B 2562/0261; A61B 5/6824; A61B 5/4356;
(Continued)

(56) References Cited

U.S. PATENT DOCUMENTS

4,781,200 A  11/1988  Baker
4,782,200 A  11/1988  Oba
(Continued)

*Primary Examiner* — Scott M. Getzow
(74) *Attorney, Agent, or Firm* — Seed Intellectual Property Law Group LLP (57) ABSTRACT

A system for assessing and monitoring a fetal electrocardiogram (ECG) and heart rate in a pregnant mother comprises wearable mechanical-electronic sensors, e.g., embedded in a wrist or arm band, which can measure mechanical pulse signals from the mother, and an abdomen patch which can measure the combined ECG signals of the fetus and mother. In another embodiment, the sensors in the wrist or arm band measure the combined fetal/maternal ECG signals, and the mother's mechanical pulse signals. By signal processing and gating out the maternal ECG signals as correlated with the mechanical maternal pulse signals, the fetal ECG and heart rate can be measured and monitored. These measurements may be displayed on the wrist or arm band device, or wirelessly through a remote device, mobile phone or computer. Sensors in the abdominal patch may also measure uterine electromyogram, uterine contractions, and fetal movements, to be correlated with the fetal ECG.

21 Claims, 6 Drawing Sheets

Related U.S. Application Data (60) Provisional application No. 62/410,712, filed on Oct. 20, 2016.

(51) Int. Cl.
*A61B 5/024* (2006.01)
*A61B 5/282* (2021.01)
*A61B 5/327* (2021.01)
*A61B 5/339* (2021.01)
*A61B 5/389* (2021.01)

(52) U.S. Cl.
CPC .......... *A61B 5/02444* (2013.01); *A61B 5/282* (2021.01); *A61B 5/327* (2021.01); *A61B 5/7235* (2013.01); *A61B 5/0011* (2013.01); *A61B 5/339* (2021.01); *A61B 5/389* (2021.01); *A61B 5/4356* (2013.01); *A61B 5/6823* (2013.01); *A61B 5/6824* (2013.01); *A61B 2562/0261* (2013.01)

(58) Field of Classification Search
CPC ......... A61B 5/0011; A61B 5/02; A61B 5/024; A61B 5/02411; A61B 5/02416–0245; A61B 5/344

See application file for complete search history.

(56) References Cited

U.S. PATENT DOCUMENTS

| | | |
|---|---|---|
| 5,042,499 A | 8/1991 | Frank et al. |
| 7,333,850 B2 | 2/2008 | Marossero et al. |
| 2014/0249436 A1* | 9/2014 | Kabakov .............. A61B 5/4325 600/509 |
| 2015/0374328 A1 | 12/2015 | Ginestet et al. |

* cited by examiner

FETAL ECG AND HEART RATE ASSESSMENT AND MONITORING DEVICE

BACKGROUND

Fetal heart rate and patterns of such can reflect the wellbeing of the fetus. There usually is an increase in fetal heart rate associated with fetal movements, and physicians have been using this association, as well as the fetal heart rate variability, to assess the wellbeing of the fetus through a test called non-stress test. Fetal heart rate responds to stress caused by uterine contractions and other factors during labor.

Intrapartum electronic fetal monitoring is based on the study of the fetal heart rate patterns. Clinicians also study the fetal heart rate response to induced uterine contractions during a contraction stress test to assess fetal wellbeing. Most of the fetal heart rate monitoring is done using non-invasive sound wave based devices on the maternal abdomen, which can have difficulties in capturing fetal heart rate during uterine contractions and maternal movements. A fetal scalp electrode to capture fetal electrocardiogram (ECG) can only be applied after the rupture of membrane of the gestational sac, and it is invasive. There is a need for a more reliable way to capture and monitor fetal heart ratenoninvasively.

DESCRIPTION OF THE RELATED ART

U.S. Pat. No. 4,782,200 describes cardiac sensors and fetal movement sensors on the mother's abdomen capturing signals for computational analysis.

U.S. Pat. No. 7,333,850 describes at least two surface sensors receiving the ECG signals of the mother and fetus for computational analysis. All of the methods described utilize computational methods to separate the maternal and fetal ECG. The effectiveness of such methods has not been promising enough to result in marketable products for measuring fetal ECG and fetal heartrate.

BRIEF SUMMARY

The present disclosure describes a novel way to utilize the signals of the maternal mechanical pulse waves, which are generated only by the cardiac contracting of the mother, to synthesize a maternal ECG, enabling the removal of the maternal ECG from the mixed maternal and fetal ECG signals captured on the abdominal skin surface, to derive the fetal ECG signals and, as desired, the fetal heart rate.

DETAILED DESCRIPTION

Disclosed herein is a method of coupling mechanical pulses of maternal heart contractions, detected with wearable sensors (e.g., in the arm or wrist areas), with maternal ECG signals—which should synchronize with the mechanical pulses—in order to remove a maternal ECG component from combined maternal and fetal ECG signals captured on the abdominal body surface to yield the fetal ECG signals and fetal heart rate. As the peripheral organs of the mother receive blood pumped from the mother's heart only, there should be no fetal mechanical pulse detectable in the maternal arm or wrist areas to confuse the isolation or extraction of fetal ECG signals.

This mechanical-electrical coupling of maternal cardiac activity as a filter to isolate or extract the fetal ECG is simpler to implement and more precise than existing methods that use rigorous mathematical signal processing to obtain a fetal ECG from a combined maternal fetal ECG signal. With the methods and devices for capturing fetal ECG and heart rate described herein, multiple applications can be devised in the field of maternal and fetal healthcare.

In at least one embodiment, described herein is a flexible unit positioned on the abdomen, flank or back area of a mother, and a separate wrist or arm band unit on the wrist or arm of the mother. Such abdominal and wrist/arm units may be constructed based on a 10-μm thick parylene C film that provides flexibility and stretchability. The circuit routings may be made of a thin film gold/titanium (0.2 μm/0.02 μm) via sputtering, for example. The electronics can be constructed, for example, using discrete surface-mount device (SMD) components or integrated inside an application specific integrated circuit (ASIC) chip.

Figure 1A:
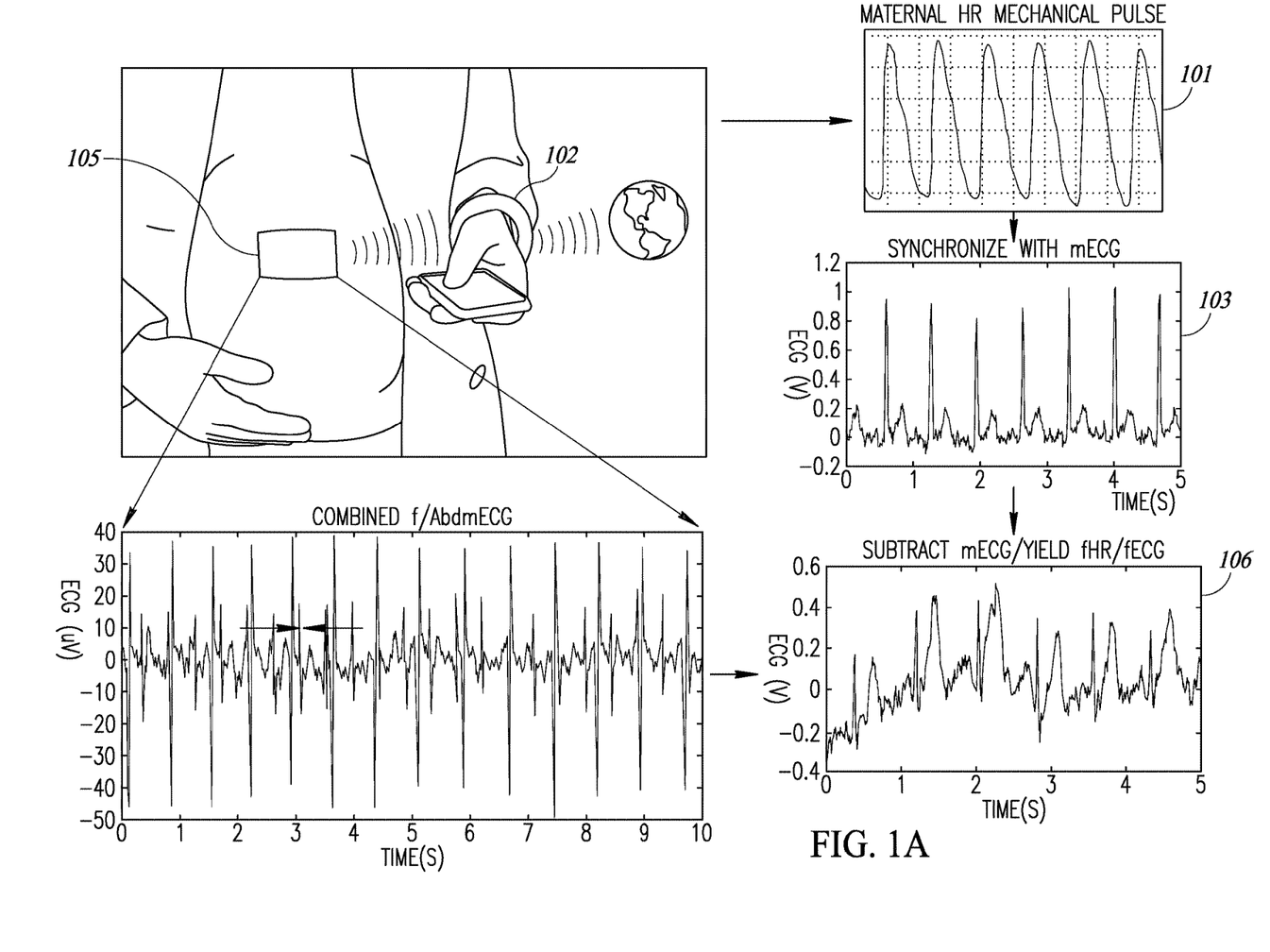
FIG. 1A illustrates at least one embodiment of a system according to the present disclosure.
Figure 3:
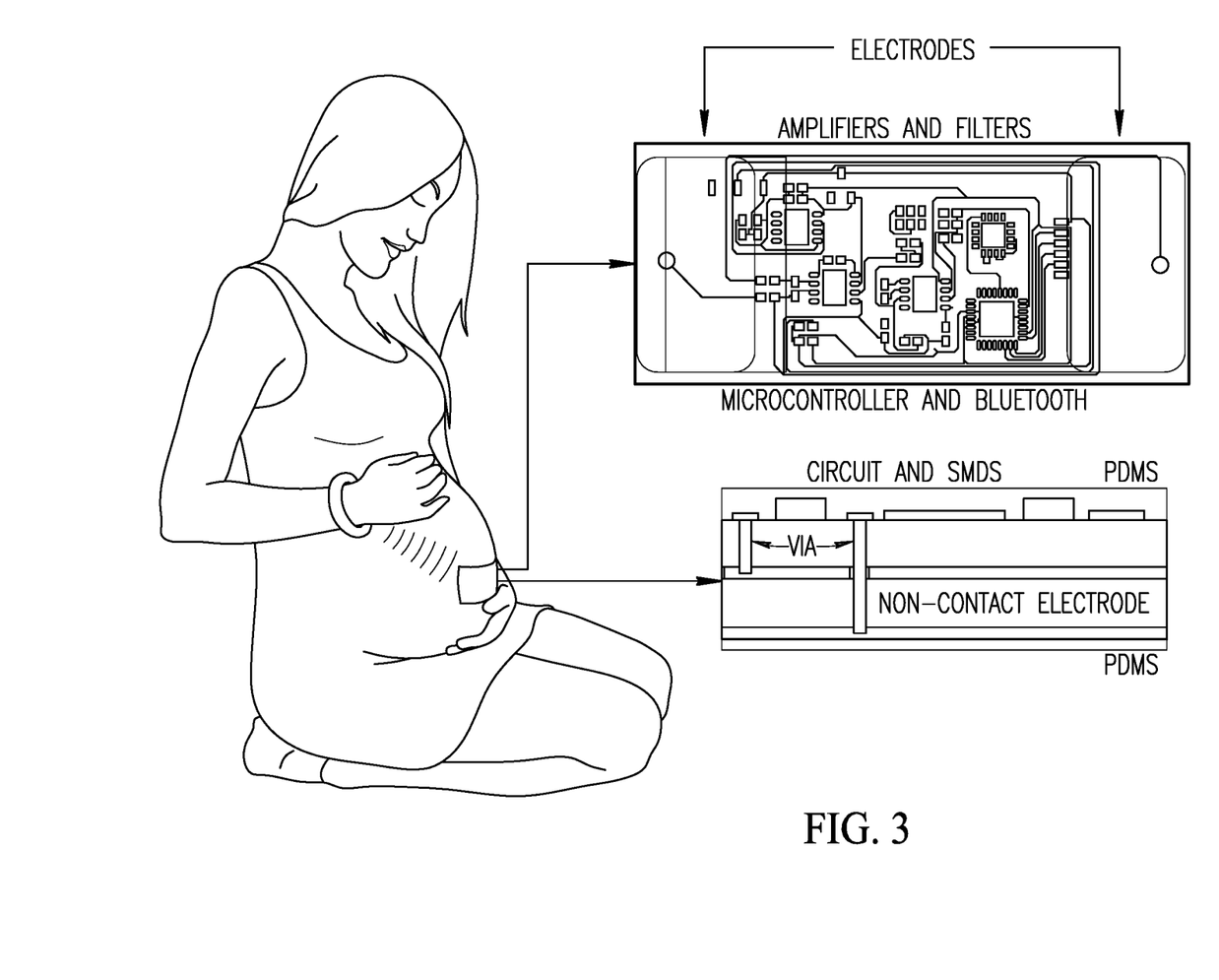
FIG. 3 illustrates an embodiment of an abdominal patch embedded with contact or non-contact ECG sensors, and mechanical-electronic sensors, for detecting fetal movement and uterine contractions with associated electronics.

An illustration of at least one embodiment of the system is shown in FIG. 1A. In FIG. 1A, an abdominal flexible unit 105 comprises electronic sensors in the form of contact or non-contact electrodes, electronics, a wireless communication chip and a battery, such as a rechargeable Li-polymer battery, configured and arranged to acquire combined fetal maternal ECG signals and transmit data wirelessly. The abdominal flexible unit 105 may be embedded in a patch or integrated inside or on a garment, body band, or mesh, for example. The electronicsmay include an instrumentation amplifier and a bandpass filter to filter out unwanted signals. For a non-contact design, after mounting the components, the entire device may be encapsulated inside polydimethylsiloxane (PDMS). The rechargeable Li-polymer battery, which is also housed inside a chamber, may remain accessible. For a contact design, the electrodes may be constructed on the other side of the electronic components, and connected by conductive vias. The side with the electronic components may be encapsulated inside PDMS. Such electrodes may be constructed using gold, and the gold electrodes may be thickened by gold electroplating, thus enhancing the performance of the skin-electrode interface. Further details depicting suitable electrodes, amplifiers and filters, and circuitry for a non-contact arrangement, in accordance with at least one embodiment, are illustrated in FIG. 3.

Figure 1B:
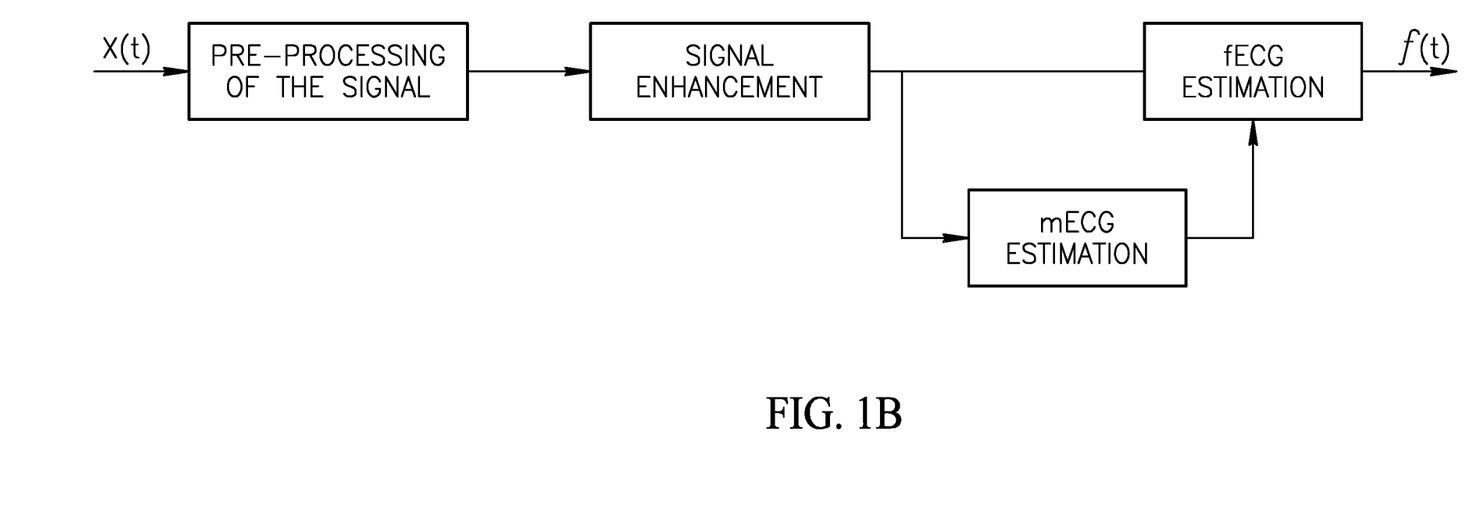
FIG. 1B illustrates a signal processing scheme that may be used with one or more embodiments of the present disclosure.
Figure 2A:
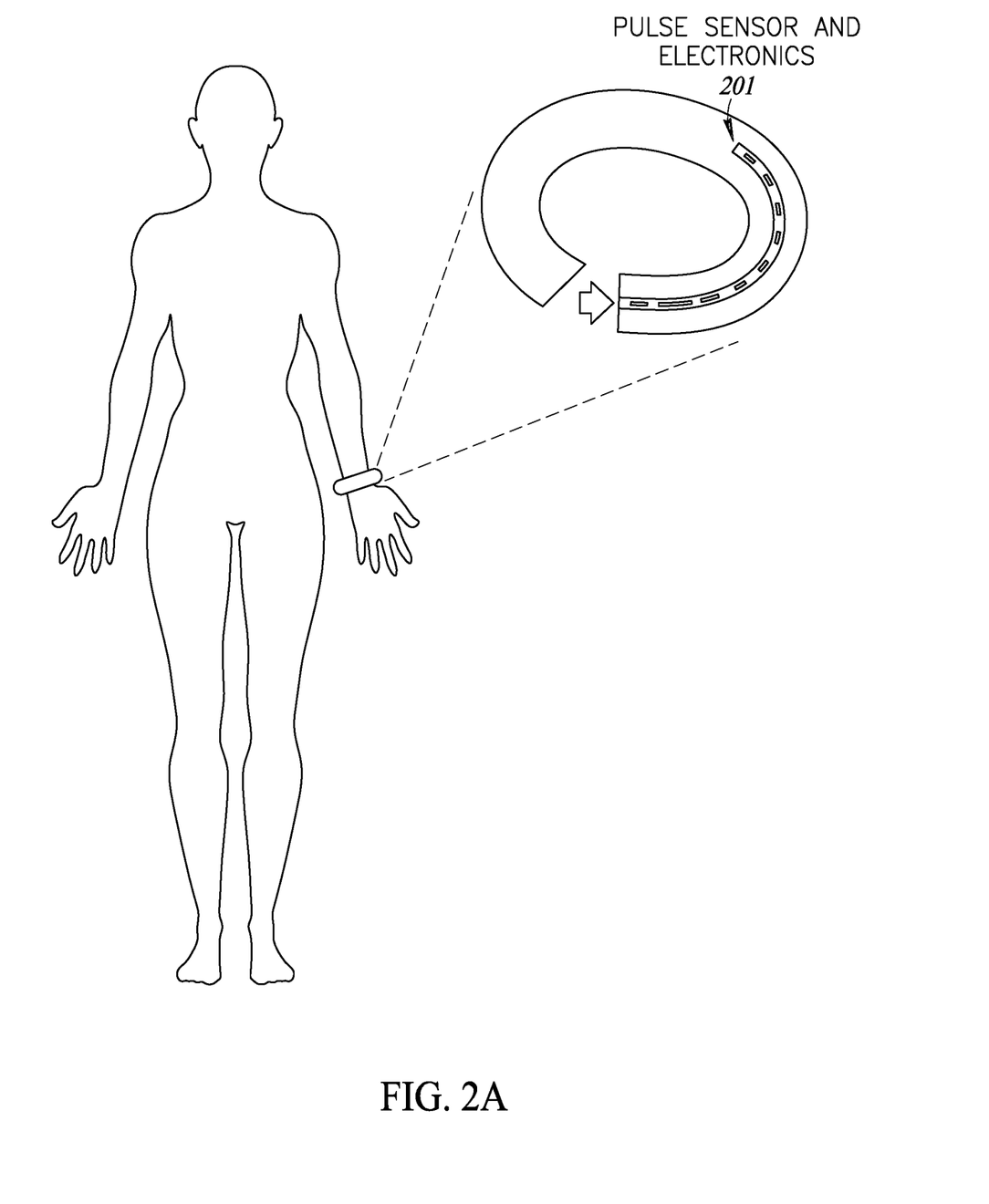
FIG. 2A illustrates an embodiment of an arterial pulse sensor embedded in a wristband with electronics, wireless communication, and a power supply.
Figure 2B:
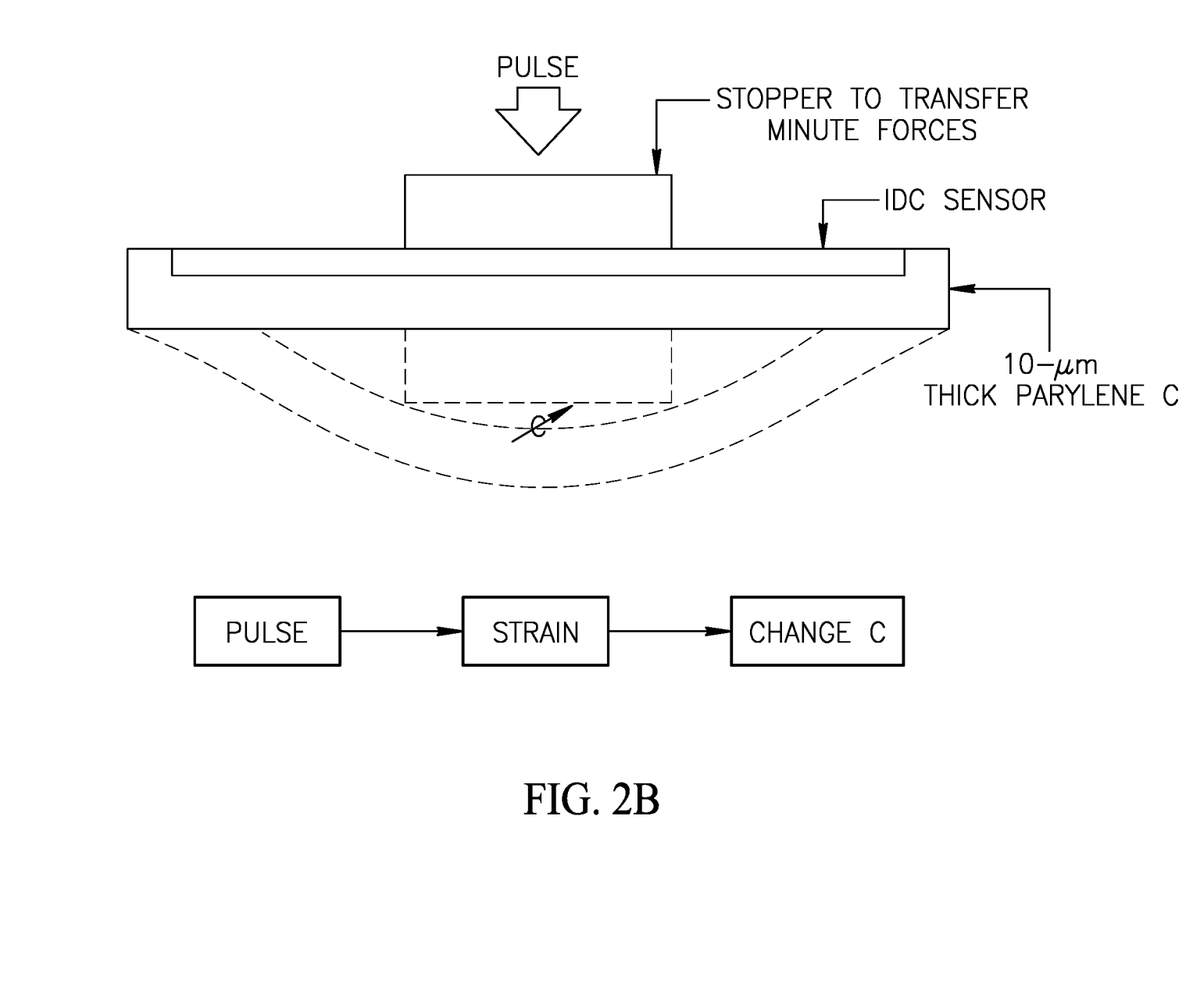
FIG. 2B illustrates a cross-sectional side view of the arterial pulse sensor of FIG. 2A in further detail, with an associated block diagram illustrating a principle of operation of the arterial pulse sensor.
Figure 2C:
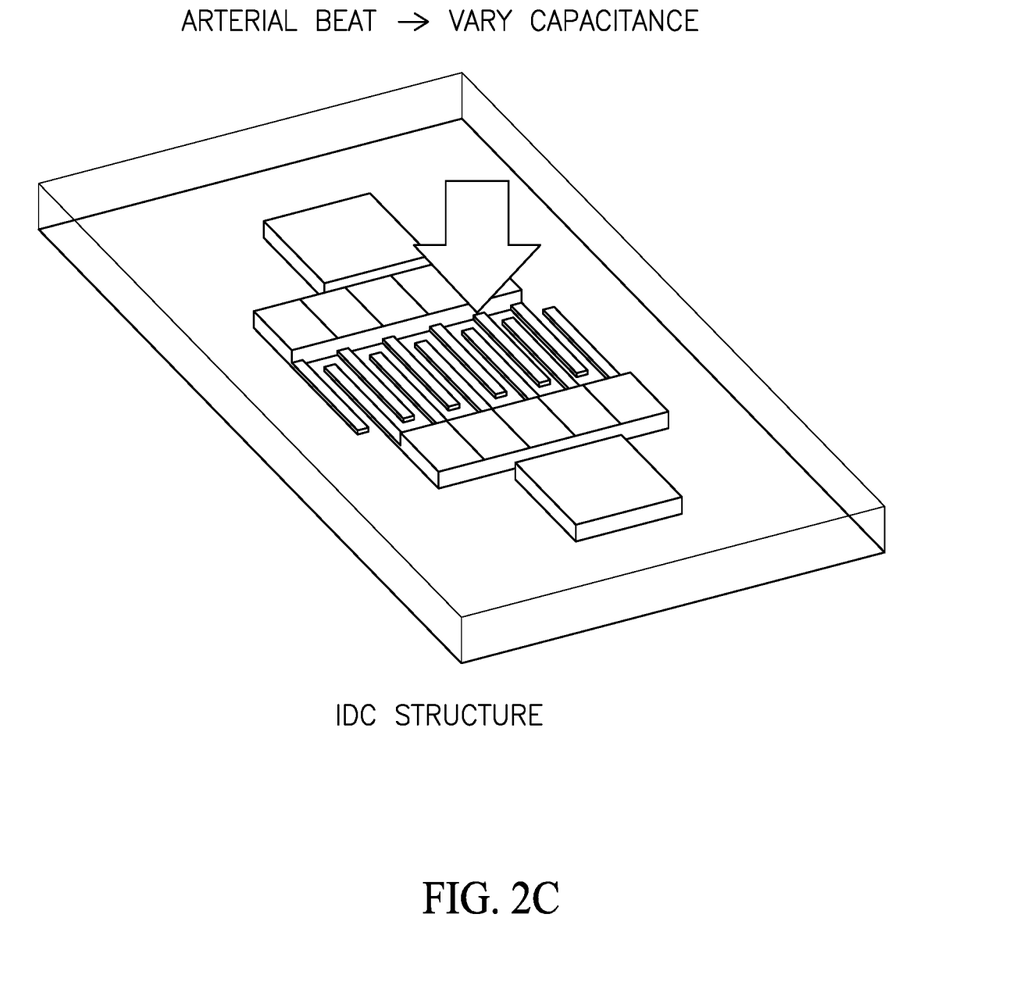
FIG. 2C illustrates a perspective view of the arterial pulse sensor of FIGS. 2A and 2B in the form of an interdigitated-finger capacitor (IDC) strain sensor.

Referring to FIGS. 2A-2C in connection with FIGS. 1A and 1B, a pulse sensor to detect a mechanical arterial pulse, a wireless chip, and embedded electronics 201 are included in the wrist or arm band unit 102 to receive/transmit and process signals from the abdominal flexibleunit 105. The pulse sensor may utilize any sensor that detects the maternal mechanical pulse generated by the local tidal change of the vascular volume resulting from cardiac contraction in the mother. A stopper (which can be constructed using a thick photoresist like SU-8) acting as a bump may be formed on the sensing area so that the contact force associated with the maternal arterial pulse can be more easily detected. For example, the pulse sensor may be made of an amorphous carbon thin film via sputtering, exhibiting a piezoresistive characteristic. The wrist pulse will deform the film, causing a change in the resistance and thus allowing the mother's pulse to be detected.

Another iteration of a maternal pulse sensor illustrated in FIG. 2A may be based on an interdigitated-finger capacitor (IDC) strain sensor as illustrated in FIGS. 2B and 2C. The stopper will transfer the minute forces from the arterial pulse to the strain sensor, resulting in capacitance changes in the IDC strain sensor. Whether the mechanical pulse sensor is resistive- or capacitive-based, the maternal mechanical pulses are picked up and synchronized with maternal ECG signals to filter out the maternal ECG component from a mixed maternal/fetal ECG to yield only the fetal ECG and fetal heart rate.

The wrist/arm unit 102 may utilize photoplethysmography (PPG) to detect the maternal pulse for the purpose of isolating or extracting the fetal ECG and heart rate as described herein. Many commercially-available smart watches that can display the heart rate of the user utilize such a photoplethysmography (PPG) technique. An iteration of the present disclosure may utilize such a smart watch or smart watch technology as a wrist unit.

While it may be more convenient to implement the present disclosure using a wrist and/or arm band where the maternal mechanical pulses are readily detectable, the same concept can be applied to other areas of the body, including the lower extremities where the maternal mechanical pulse can also be detected in multiple areas such as the ankle, dorsum of the foot, and the femoral region.

FIG. 1B illustrates a signal processing scheme that may be used with one or more embodiments of the present disclosure. Using the mechanical maternal pulse signals 101 detected by the sensors in the arm or wrist band 102, a maternal ECG signal component may be synthesized and removed from the combined maternal fetal ECG signals captured on the surface of the body or extremities. The synthesized maternal ECG is time-matched 103 to the combined maternal fetal ECG based on the maternal vascular volume pulse signals and subtracted out 106 of the combined maternal fetal ECG, leaving only the fetal ECG signals to be de-noised, displayed or transmitted. Since the combined maternal fetal ECG contains both fetal and maternal heart rhythms at different frequencies, without additional information it is difficult for existing processing systems or programs to determine the correct R-R intervals of each of the maternal and fetal components. By obtaining the maternal mechanical pulse information as described herein, which has the same time period as the R-R interval of the maternal ECG component in the combined ECG, the maternal ECG component can be synthesized and subtracted from the combined maternal fetal ECG signal by either analog or digital processing, e.g., in the wrist unit 102 or elsewhere.

For example, with the known maternal heart rate as identified by detection of the maternal mechanical pulse, a maternal ECG signal in at least one embodiment can be synthesized by the ECG Dynamic Model. The ECG Dynamic Model represents an ECG signal by a sum of five Gaussian functions, with each function corresponding to the five standard waves of an ECG signal, W={P,Q,R,S,T}. By synthesizing the maternal ECG, the fetal ECG can be isolated or extracted from the combined abdominal maternal fetal ECG signal via an algorithm, such as a Least Mean Square (LMS) adaptive filter or an Extended Kalman Filter (EKF), that subtracts the synthesized maternal ECG component or otherwise filters the synthesized maternal ECG component from the combined abdominal fetal maternal ECG signal. Such signal processing can be integrated in the processing circuitry of the wrist band or be cloud-based computed.

The foregoing provides a novel way to separate out fetal ECG signals, leveraging the maternal mechanical pulse signals, from the combined fetal maternal ECG signals detected by the sensors on the mother's body. Thus following pre-processing and enhancement of the combined maternal fetal ECG and estimation (e.g., synthesis) of the maternal ECG (mECG) using the detected and synchronized maternal mechanical pulse, an estimation of the fetal ECG (fECG) is obtained by subtracting the mECG from the combined maternal fetal ECG. In this manner, the system of the present disclosure extracts the fECG while avoiding the complicated signal processing that has been used in various prior attempts to separate the fetal and maternal ECG signals.

While the sensors in the arm or wrist band 102, or on the abdomen, flank and back areas 105 can all capture the combined maternal fetal ECG signals, using the abdominal sensors 105 has several advantages. First, the sensors on the abdomen are more likely to capture the strongest fetal ECG signals due to their proximity to the fetal source. Second, other sensors can be placed with the ECG sensors on the abdomen to capture information on fetal movements, uterine contractions, and uterine electromyogram (EMG). Correlating the fetal heat rates with fetal movements and uterine contractions is useful in assessing fetal wellbeing using the non-stresstest, contraction stress test, and intrapartum fetal monitoring.

One example of an embodiment that implements the non-stress test using the system disclosed herein uses a mobile phone, and may further include use of cloud computing. The fetal ECG signals and a fetal heart rate tracing obtained using the present disclosure are transmitted wirelessly to the mobile phone, with the option of uploading the information to the cloud. Uterine contractions and fetal movements can be detected objectively by the sensors in the abdominal patch unit, or indicated by the mother, after feeling such contractions or movements, by pressing or otherwise activating indicators in an app that is executing in the mobile phone. In the event of a uterine contraction or fetal movement, the fetal heart rate tracing should typically show a reactive acceleration of the fetal heart rate during and right after the event. Signal processing in the mobile phone or accessible through cloud computing may be used to assess the fetal heart rate response to see whether it is within the range of a predetermined normal response, and if needed, to alert the mother through the mobile phone app or the clinicians monitoring the patient through the mobile phone network or the cloud. Similarly, the baseline fetal heart rate, and the heart rate variabilities can be analyzed and monitored through the system. The fetal heart ratevariabilities, including a heart rate increase that occurs with fetal movements or uterine contractions, can be used to help assess the fetal developmental/health status. In a contraction stress test, where uterine contraction is induced with medications, the fetal heart rate patterns in response to the contractions can also serve to assess fetal well-being. The fetal heart rate response is correlated with the uterine contractions for assessment of fetal wellbeing as described in the embodiment for the non-stress test.

During labor, it is a common clinical practice to monitor the fetus and mother with a cardiotocograph (CTG), which is a continuous record of the fetal heart rate obtained by an ultrasound transducer placed on the mother's abdomen, with a second transducer placed over the uterine fundus to simultaneously record uterine activity. The fetal heart rate, its variability, and response to uterine contractions help guide the clinician to assess the status of the fetus and manage the labor and delivery. However, an ultrasound transducer often has difficulty functioning consistently due to sensitive placement requirements and frequent interference from maternal and fetal movements and uterine contractions. Improper or inconsistent data produced by an ultrasound transducer can be a constant source of confusion, even frustration, for clinicians. A scalp fetal ECG will produce more reliable information, but it can only be placed after rupture of the membrane, and it is invasive to the fetus and causes parental concerns. The fetal ECG and heart rate capture using the system described in the present disclosure is non-invasive, consistent, and precise, before and during labor and delivery.

Another advantage of the system disclosed herein is its portability. Both the arm or wrist band and the abdominal patch are small and unobtrusive. Using the wireless technology to connect the arm or wrist band, the abdominal patch, and a mobile phone to capture all the needed information, the system is mobile and convenient both before and during labor. Since mobile phone service is increasingly available worldwide, even in the most resource poor environments, the system disclosed herein impacts the delivery of maternal and child healthcare for even remote and resource poor populations. Linking pregnant mothers in those populations with a mobile phone directly or via cloud computing to a remote healthcare provider will help to greatly improve the delivery of obstetrical care to underserved populations. The simple-to-use system disclosed herein can be easily deployed, even by lay people with minimal training.

As previously described, embodiments of the present system are capable of isolating or extracting the fetal ECG and deriving the fetal heart rate from a mixed maternal fetal ECG signal by synthesizing a maternal ECG based on the maternal mechanical volume pulse at the mother's wrist, and after time matching the synthesized maternal ECG with the mixed maternal fetal ECG, subtracting the synthesized maternal ECG from the mixed maternal fetal ECG. As an example to illustrate the simplicity of use of the present system, an iteration of the system may utilize one of many existing smart wristwatches that measure and display a person's heart rate by assessing the person's mechanical pulses at the wrist using photoplethysmography (PPG). Most people would find it just as simple to read the fetal heart rate displayed in the same fashion as with a regular heart rate monitoring wristwatch. With the ability to capture high-quality fetal ECG using the methods and devices disclosed herein, the morphology of the fetal ECG can be analyzed within the system or remotely through cloud computing technology. This is useful to assess the fetal cardiac status and health status of the fetus, and also to monitor the fetus remotely, especially for a fetus at risk.

As discussed previously in connection with FIG. 1B, the blood at a peripheral organ of the mother is pumped only from the mother's heart. Accordingly, maternal mechanical pulses 101 captured by a pulse sensor in the wristband 102 are matched (i.e., synchronized) to the combined maternal fetal ECG signal 104 captured by the ECG sensors on the mother's body 105 or wrist 102 and a maternal ECG component is synthesized based on the maternal heart rate derived from the maternal mechanical pulses. After the maternal ECG component 103 is synthesized, the maternal ECG component is subtracted from the combined maternal fetal ECG signal 106, yielding the fetal ECG signal component.

FIG. 2A illustrates an embodiment of the pulse sensor 201 in the wrist band with electronics for data processing, wireless communication, and power supply. In at least one embodiment, as illustrated in FIG. 2B, the wristband is based on a piece of PDMS encapsulating parylene C film with gold electrodes and routings, as well as electronic component, as described above.

FIG. 3 illustrates an embodiment of an abdominal patch embedded with contact or non-contact ECG sensors, and also mechanical-electronic sensors for detecting fetal movement and uterine contractions with associated electronics. The abdominal patch may be constructed similar to the wrist or arm unit with flexible electronics.

Thus in at least one embodiment, a system constructed according to the present disclosure may include a pulse sensor positioned in a wrist or arm band, wherein the pulse sensor is configured and arranged to capture a maternal mechanical pulse signal of a mother. The system further includes electronic sensors configured and arranged for application to the abdomen, flank or back of the mother to capture a combined maternal and fetal ECG signal. The combined maternal and fetal ECG signal includes a maternal ECG component due to electrical activity of the mother's heart and a fetal ECG component due to electrical activity of the heart of a fetus in the mother. In addition, the system includes processing circuitry configured and arranged to process the maternal mechanical pulse signal and the combined maternal and fetal ECG signal to isolate the fetal ECG component from the combined maternal and fetal ECG signal by synthesizing the maternal ECG component based on the maternal mechanical pulse signal and using a timing of the maternal mechanical pulse signal to extract or remove the synthesized maternal ECG component from the combined maternal and fetal ECG signal and yield the fetal ECG component.

The system may further comprise a display in the wrist or arm band, wherein the fetal ECG component and/or a fetal heart rate derived from the fetal ECG component are displayed on the wrist or arm band. Alternatively or in addition, the system may further comprising a mobile device (e.g., as illustrated in FIG. 1A), wherein the fetal ECG component and/or a fetal heart rate derived from the fetal ECG component are transmitted wirelessly to the mobile device. Alternatively or in addition, the system may further comprise a remote computer, wherein the fetal ECG component and/or a fetal heart rate derived from the fetal ECG component are transmitted wirelessly to the remote computer.

In at least one embodiment, the processing circuitry is housed in a computing device separate from the pulse sensor and the electronic sensor. Measurements of the maternal mechanical pulse signal and the combined maternal and fetal ECG signal are transmitted wirelessly to the computing device for processing to isolate the fetal ECG component. The processing circuitry may assess a fetal heart rate response based on the fetal ECG component and/or a fetal heart rate derived from the fetal ECG component and determine whether the fetal heart rate response is within a range of a predetermined normal response and if not, the processing circuitry is configured to alert the mother or a clinician monitoring the mother.

The system may further comprising electronic-mechanical sensors that are embedded in an abdominal patch with the electronic sensors that capture the combined maternal and fetal ECG signal (e.g., as illustrated in FIG. 3). The electronic-mechanical sensors are configured and arranged to measure uterine contractions, uterine electromyographic (EMG) signals, and/or fetal movement. Measurements of the uterine contractions, uterine EMG, and/or fetal movement may be transmitted wirelessly and communicated with electronics in the arm or wrist band.

The pulse sensor that captures the maternal mechanical pulse signal may use photoplethysmography (PPG), a carbon piezoresistive sensor, or an interdigitated-finger capacitor (IDC) strain sensor (e.g., as illustrated in FIG. 2C) to detect the maternal mechanical pulse signal.

In yet one or more other embodiments, a system constructed according to the present disclosure includes a mechanical sensor configured and arranged to capture a maternal mechanical pulse signal of a mother; one or more electronic sensors configured and arranged to capture a combined maternal and fetal ECG signal in the mother; and processing circuitry configured and arranged to isolate a fetal ECG component in the combined maternal and fetal ECG signal by removing (e.g., subtracting) a synthesized maternal ECG component from the combined maternal and fetal ECG signal, wherein the maternal ECG component is synthesized and removed from the combined maternal and fetal ECG signal using information derived from the maternal mechanical pulse signal.

The mechanical sensor, which may be an arterial pulse sensor, may be embedded in wrist or arm band that is applied to the wrist or arm of the mother, as described earlier herein. The mechanical sensor may detect the maternal mechanical pulse signal using photoplethysmography (PPG), a carbon piezoresistive sensor, or an interdigitated-finger capacitor (IDC) strain sensor. The one or more electronic sensors that capture the combined maternal and fetal ECG signal in the mother may be embedded in a patch applied to the abdomen, flank or back of the mother.

The system may further comprise a display device that wirelessly receives and displays the fetal ECG component or fetal heart rate information derived from the fetal ECG component. Alternatively or in addition, the system may further comprising a memory in which the fetal ECG component and/or fetal heart rate information derived from the fetal ECG component are recorded. The memory may be implemented in the write or arm band, a mobile phone or other computing device.

The various embodiments described above can be combined to provide further embodiments. All of the U.S. patents referred to in this specification are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system comprising:
 a mechanical sensor configured and arranged to capture a maternal mechanical pulse signal of a mother;
 one or more electronic sensors configured and arranged to capture a combined maternal and fetal ECG signal in the mother, wherein the combined maternal and fetal ECG signal includes a maternal ECG component due to electrical activity of the mother's heart and a fetal ECG component due to electrical activity of the heart of a fetus in the mother; and
 processing circuitry configured and arranged to isolate the fetal ECG component from the combined maternal and fetal ECG signal by using information derived from the maternal mechanical pulse signal to synthesize a synthesized maternal ECG component and remove the synthesized maternal ECG component from the combined maternal and fetal ECG signal.

2. The system of claim 1, wherein the mechanical sensor is embedded in a wrist or armband applied to the mother.

3. The system of claim 2, wherein the mechanical sensor is an arterial pulse sensor.

4. The system of claim 1, wherein the one or more electronic sensors are embedded in a patch applied to the abdomen, flank or back of the mother.

5. The system of claim 1, further comprising a display device configured and arranged to wirelessly receive and display the fetal ECG component and/or fetal heart rate information derived from the fetal ECG component.

6. The system of claim 1, wherein the processing circuitry is configured and arranged to record the fetal ECG component and/or fetal heart rate information derived from the fetal ECG component in a memory.

7. The system of claim 1, wherein the mechanical sensor captures the maternal mechanical pulse signal using photoplethysmography (PPG), a carbon piezoresistive sensor, or an interdigitated-finger capacitor (IDC) strain sensor.

8. A system comprising:
 a pulse sensor configured and arranged to capture a cardiac pulse signal of a mother;
 one or more sensors configured and arranged to capture a combined maternal and fetal ECG signal that includes a maternal ECG component and a fetal ECG component, wherein the maternal ECG component represents electrical activity of the mother's heart and the fetal ECG component represents electrical activity of the heart of a fetus in the mother; and
 processing circuitry configured and arranged to:
  determine the maternal ECG component from the cardiac pulse signal of the mother, and
  using a timing parameter derived from the cardiac pulse signal of the mother, remove the determined maternal ECG component from the combined maternal and fetal ECG signal to isolate the fetal ECG component.

9. The system of claim 8, further comprising a display device, wherein the fetal ECG component and/or a fetal heart rate derived from the fetal ECG component are displayed on the display device.

10. The system of claim 8, further comprising communications circuitry configured and arranged to wirelessly transmit the fetal ECG component and/or a fetal heart rate derived from the fetal ECG component to a mobile device.

11. The system of claim 8, further comprising communications circuitry configured and arranged to wirelessly transmit the fetal ECG component and/or a fetal heart rate derived from the fetal ECG component to a remote computer.

12. The system of claim 8, wherein the processing circuitry is separate from the pulse sensor, the system further comprising communications circuitry configured and arranged to wirelessly transmit the cardiac pulse signal of the mother to the processing circuitry.

13. The system of claim 8, wherein the processing circuitry is separate from the one or more electronic sensors, the system further comprising communications circuitry configured and arranged to wirelessly transmit the combined maternal and fetal ECG signal to the processing circuitry.

14. The system of claim 8, wherein the processing circuitry is configured to determine a fetal heart rate response based on the isolated fetal ECG component.

15. The system of claim 14, wherein the processing circuitry is configured to determine whether the fetal heart rate response is within a range of a predetermined normal response and if not, the processing circuitry is configured to alert the mother or a clinician monitoring the mother.

16. The system of claim 8, further comprising electronic-mechanical sensors that are embedded in an abdominal patch with the one or more electronic sensors that capture the combined maternal and fetal ECG signal, wherein the electronic-mechanical sensors are configured to measure uterine contractions, uterine electromyographic (EMG) signals, and/or fetal movement, and communicate said measurements to the processing circuitry.

17. The system of claim 8, wherein the pulse sensor is configured to use photoplethysmography (PPG), a carbon piezoresistive sensor, or an interdigitated-finger capacitor (IDC) strain sensor to capture the cardiac pulse signal of the mother.

18. A method comprising:
capturing a maternal pulse signal of a mother;
capturing a combined maternal and fetal ECG signal in the mother, wherein the combined maternal and fetal ECG signal includes a maternal ECG component due to electrical activity of the mother's heart and a fetal ECG component due to electrical activity of the heart of a fetus in the mother; and
synthesizing a synthesized maternal ECG component using information derived from the captured maternal pulse signal; and
removing the synthesized maternal ECG component from the combined maternal and fetal ECG signal using information derived from the captured maternal pulse signal to isolate the fetal ECG component.

19. The method of claim 18, wherein the synthesized maternal ECG component is removed from the combined maternal and fetal ECG signal using a timing parameter derived from the captured maternal pulse signal.

20. The method of claim 18, further comprising wirelessly transmitting the fetal ECG component and/or a fetal heart rate derived from the fetal ECG component to a mobile device operated by the mother or a clinician monitoring the mother.

21. The method of claim 18, further comprising:
determining a fetal heart rate response based on the isolated fetal ECG component; and
determining whether the fetal heart rate response is within a range of a predetermined normal response and if not, alerting the mother or a clinician monitoring the mother.

* * * * *